US009241659B2

(12) United States Patent
Rompa, Jr. et al.

(10) Patent No.: US 9,241,659 B2
(45) Date of Patent: Jan. 26, 2016

(54) SYSTEMS AND METHODS FOR TRANSDERMAL SECRETION DETECTION

(71) Applicant: BI Incorporated, Boulder, CO (US)

(72) Inventors: Victor J. Rompa, Jr., Westminster, CO (US); Hollis Pence, Lakewood, CO (US); Timothy D. Waters, Boulder, CO (US); Todd Bloemendaal, Lakewood, CO (US); Arthur P. Newsome, Johnstown, CO (US)

(73) Assignee: BI Incorporated, Boulder, CO (US)

( * ) Notice: Subject to any disclaimer, the term of this patent is extended or adjusted under 35 U.S.C. 154(b) by 0 days.

(21) Appl. No.: 14/150,927

(22) Filed: Jan. 9, 2014

(65) Prior Publication Data

US 2014/0128693 A1   May 8, 2014

Related U.S. Application Data

(63) Continuation of application No. 12/716,254, filed on Mar. 2, 2010, now Pat. No. 8,657,744.

(60) Provisional application No. 61/162,638, filed on Mar. 23, 2009.

(51) Int. Cl.
| | |
|---|---|
| *A61B 5/00* | (2006.01) |
| *A61B 5/145* | (2006.01) |
| *A61B 5/1477* | (2006.01) |
| *A61B 5/11* | (2006.01) |

(52) U.S. Cl.
CPC ............... *A61B 5/145* (2013.01); *A61B 5/1477* (2013.01); *A61B 5/14542* (2013.01); *A61B 5/6801* (2013.01); *A61B 5/6828* (2013.01); *A61B 5/6831* (2013.01); *A61B 5/6844* (2013.01); *A61B 5/6886* (2013.01); *A61B 5/1112* (2013.01); *A61B 2560/0276* (2013.01); *A61B 2560/04* (2013.01); *A61B 2560/0406* (2013.01); *A61B 2560/0462* (2013.01); *A61B 2560/06* (2013.01)

(58) Field of Classification Search
USPC ............ 600/309; 180/272; 73/23.3; 340/576
See application file for complete search history.

(56) References Cited

U.S. PATENT DOCUMENTS

| | | | | | |
|---|---|---|---|---|---|
| 4,678,057 | A | * | 7/1987 | Elfman et al. ................ | 180/272 |
| 4,809,810 | A | * | 3/1989 | Elfman et al. ................ | 180/272 |
| 4,902,628 | A | * | 2/1990 | Blair ............................ | 436/132 |
| 5,261,596 | A | * | 11/1993 | Tachibana et al. ........... | 236/49.3 |
| 5,597,534 | A | * | 1/1997 | Kaiser ........................ | 422/82.02 |
| 5,788,833 | A | * | 8/1998 | Lewis et al. .................... | 205/787 |
| 5,830,132 | A | * | 11/1998 | Robinson ....................... | 600/310 |
| 5,891,398 | A | * | 4/1999 | Lewis et al. ................. | 422/82.02 |
| 5,944,661 | A | * | 8/1999 | Swette et al. ................. | 600/345 |
| 7,031,778 | B2 | * | 4/2006 | Hsiung et al. ................... | 700/29 |
| 7,299,890 | B2 | * | 11/2007 | Mobley et al. ................ | 180/272 |
| 7,403,804 | B2 | * | 7/2008 | Ridder et al. ................. | 600/310 |
| 7,413,047 | B2 | * | 8/2008 | Brown et al. ................. | 180/272 |
| 7,451,852 | B2 | * | 11/2008 | Stewart et al. ................ | 180/272 |

(Continued)

*Primary Examiner* — Clayton E Laballe
*Assistant Examiner* — Warren K Fenwick
(74) *Attorney, Agent, or Firm* — Hamilton DeSanctis & Cha

(57) ABSTRACT

Various embodiments of the present invention provide systems and methods for detecting chemicals. As an example, a system is disclosed that includes a chemical sensor, a processor, and a computer readable medium. The computer readable medium includes instructions executable by the processor to: receive a plurality of outputs from the chemical sensor; calculate a baseline value using the plurality of outputs from the chemical sensor; and report an event when the baseline value is exceeded.

23 Claims, 11 Drawing Sheets

(56) References Cited

U.S. PATENT DOCUMENTS

| | | | |
|---|---|---|---|
| 7,481,292 B2* | 1/2009 | Mobley et al. | 180/272 |
| 7,756,558 B2* | 7/2010 | Ridder et al. | 600/310 |
| 7,916,283 B2* | 3/2011 | Fukutani et al. | 356/73 |
| 7,930,927 B2* | 4/2011 | Cooper et al. | 73/53.01 |
| 8,095,193 B2* | 1/2012 | Ridder et al. | 600/310 |
| 8,657,744 B2* | 2/2014 | Rompa et al. | 600/309 |
| 2006/0173256 A1* | 8/2006 | Ridder et al. | 600/316 |
| 2006/0237253 A1* | 10/2006 | Mobley et al. | 180/272 |
| 2008/0216561 A1* | 9/2008 | Cooper et al. | 73/53.01 |
| 2009/0099426 A1* | 4/2009 | Sachanandani et al. | 600/301 |
| 2011/0018726 A1* | 1/2011 | Gonzales | 340/628 |
| 2011/0154887 A1* | 6/2011 | Cooper et al. | 73/53.01 |
| 2012/0078473 A1* | 3/2012 | Ridder et al. | 701/45 |

* cited by examiner

SYSTEMS AND METHODS FOR TRANSDERMAL SECRETION DETECTION

CROSS REFERENCE TO RELATED APPLICATION

The present application is a continuation of U.S. patent application Ser. No. 12/716,254 entitled "Systems and Methods for Transdermal Secretion Detection", and filed Mar. 2, 2010 by Rompa et al.; which itself claims priority to (i.e., is a non-provisional of) U.S. Pat. App. No. 61/162,638 entitled "Systems and Methods for Detecting Transdermal Secretions of Trace Chemicals While Eliminating Environmental Factors, Normal Human Intervention, and/or Deliberate Attempts to Avoid Detection", and filed Mar. 23, 2009 by Rompa et al. The entirety of both of the aforementioned applications is incorporated herein by reference for all purposes.

BACKGROUND OF THE INVENTION

The present invention is related to chemical detection, and in particular to systems and methods for detecting transdermal secretions.

Large numbers of individuals are currently housed in prisons. This represents a significant cost to society both in terms of housing expense and wasted productivity. To address this concern, house arrest systems have been developed for use by less violent offenders. This allows the less violent offender to be monitored outside of a traditional prison system and allows the offender an opportunity to work and interact to at least some degree in society. The same approach is applied to paroled prisoners allowing for a monitored transition between a prison atmosphere and returning to society.

In some cases, it is not practical to parole an offender because they suffer from an alcohol addiction that may lead to the same activity that lead to their original incarceration. Present approaches to monitor alcohol consumption costly, time consuming and in some cases, impractical. In other cases, the terms of an individual's parole may include a requirement that the individual abstain from the use of alcohol, but monitoring adherence to such terms is costly and time consuming. In yet other circumstances, it may be possible that an individual could avoid incarceration altogether if they agree to abstain from the use of alcohol. Again, assuring adherence to such terms is at best costly and time consuming.

Griner Inc. of Newton, Mass. has developed a product that includes a transdermal alcohol monitor with a strap allowing it to be placed around the leg of an individual being monitored. Such an approach offers some hope in portable alcohol monitoring. Unfortunately, the strap has to be maintained relatively tight to assure reasonable reading. Such is not always possible due to the movement of the individual being monitored. In some cases, such movement reduced the accuracy of any readings and in some cases results in an inability to rely on the readings. Further, such a device is not easily serviceable and may be susceptible to tampering by the monitored individual.

Thus, for at least the aforementioned reasons, there exists a need in the art for more advanced approaches, devices and systems for detecting alcohol usage by an individual.

BRIEF SUMMARY OF THE INVENTION

The present invention is related to chemical detection, and in particular to systems and methods for detecting transdermal secretions.

Some embodiments of the present invention provide portable alcohol monitoring devices. Such devices include a device body, an alcohol sensor, and a liquid cartridge. The alcohol sensor is associated with the device body, and relies on a liquid supply to perform an alcohol measurement on a subject. The liquid cartridge is replaceably coupled to the device body and provides the liquid supply to the alcohol sensor. In some instances of the aforementioned embodiments, the liquid cartridge is filled with water. In one particular instance, the water is distilled, de-ionized water. The liquid cartridge may be, but is not limited to, a cylindrical cartridge, or a cubical cartridge.

In some instances of the aforementioned embodiments, the alcohol monitoring devices further include a securing device that is operable to secure the device body to the subject. In various instances of the aforementioned embodiments, the alcohol sensor is incorporated in the device body, and a force element presses the alcohol sensor toward the subject. As one example, the force element may be a spring and the alcohol sensor may be coupled to the device body via a bellows. In other instances, the device body includes an electronics body and a sensor body with the sensor body encasing the alcohol sensor and being attached to the electronics body via a torsion hinge. In such cases, the torsion hinge operates to press the alcohol sensor toward the subject.

In some instances of the aforementioned embodiments, the liquid cartridge is coupled to the body device using tamper resistant hardware. In some cases, the tamper resistant hardware is designed such that it is damaged upon replacement of the liquid cartridge. As just some examples, the tamper resistant hardware may be, but is not limited to, a tamper resistant cap, and a tamper resistant screw. In particular instances of the aforementioned embodiments, the device further includes a proximity detector that is operable to detect whether the device body is within a desired proximity of the subject. Further, in some instances of the aforementioned embodiments, the device further includes at least one tamper sensor that is operable to detect unauthorized tampering with the device.

Other embodiments of the present invention provide portable alcohol monitoring devices that include a device body, an alcohol sensor that is associated with the device body, a securing device that is operable to secure the device body to the subject, and a force element that is operable to press the alcohol sensor toward the subject.

Yet other embodiments of the present invention provide methods for maintaining alcohol monitoring equipment. Such methods include providing a portable alcohol monitoring device having a device body, an alcohol sensor, and a liquid cartridge. The alcohol sensor is associated with the device body, and relies on a liquid supply to perform an alcohol measurement on a subject. The liquid cartridge is replaceably coupled to the device body and provides the liquid supply to the alcohol sensor. The methods further include removing a tamper resistant hardware element, and in doing so damaging the tamper resistant hardware element. Further, the methods include removing and replacing the liquid cartridge, and replacing the tamper resistant hardware. In some cases, the replacing the liquid cartridge includes refilling an existing liquid cartridge and replacing it, while in other cases replacing the liquid cartridge includes using a different liquid cartridge.

This summary provides only a general outline of some embodiments according to the present invention. Many other objects, features, advantages and other embodiments of the present invention will become more fully apparent from the following detailed description, the appended claims and the accompanying drawings and figures.

BRIEF DESCRIPTION OF THE DRAWINGS

A further understanding of the various embodiments of the present invention may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

The present invention is related to chemical detection, and in particular to systems and methods for detecting transdermal secretions.

Some embodiments of the present invention provide portable alcohol monitoring devices. Such devices include a device body, an alcohol sensor, and a liquid cartridge. As sued herein, the phrase "device body" is used in its broadest sense to mean a portion of a device including hardware for performing one or more functions. In some cases, the device body may be a case holding one or more functional elements, while in other cases, the device body includes two or more cases with each holding functional elements. In the aforementioned embodiments, the alcohol sensor is associated with the device body, and relies on a liquid supply to perform an alcohol measurement on a subject. The liquid cartridge is replaceably coupled to the device body and provides the liquid supply to the alcohol sensor. As used herein, the phrase "liquid cartridge" is used in its broadest sense to mean any container capable of holding a liquid.

In some instances of the aforementioned embodiments, the alcohol monitoring devices further include a securing device that is operable to secure the device body to the subject. In various instances of the aforementioned embodiments, the alcohol sensor is incorporated in the device body, and a force element presses the alcohol sensor toward the subject. As used herein, the phrase "force element" is used in its broadest sense to mean an element capable of providing some level of force to an object. As one example, the force element may be a spring and the alcohol sensor may be coupled to the device body via a bellows. As another example, the force element may be a torsion spring.

In some instances of the aforementioned embodiments, the liquid cartridge is filled with water. In one particular instance, the water is distilled, de-ionized water. The liquid cartridge may be, but is not limited to, a cylindrical cartridge, or a cubical cartridge. As used herein, the phrase "cubicle cartridge" is used in its broadest sense to mean any container having the general shape of a cube where the length of the container sides are not necessarily equal. Similarly, the phrase "cylindrical cartridge" is used in its broadest sense to mean any container having he general shape of a cylinder.

In some instances of the aforementioned embodiments, the liquid cartridge is coupled to the body device using tamper resistant hardware. As used herein, the phrase "tamper resistant hardware" is used in its broadest sense to mean any hardware element that provides some indication of tampering when it has been tampered with. In some cases, the tamper resistant hardware is designed such that it is damaged upon replacement of the liquid cartridge. Such damage may be in some cases, irreparable damage. As just some examples, the tamper resistant hardware may be, but is not limited to, a tamper resistant cap, and a tamper resistant screw.

Figure 1A:
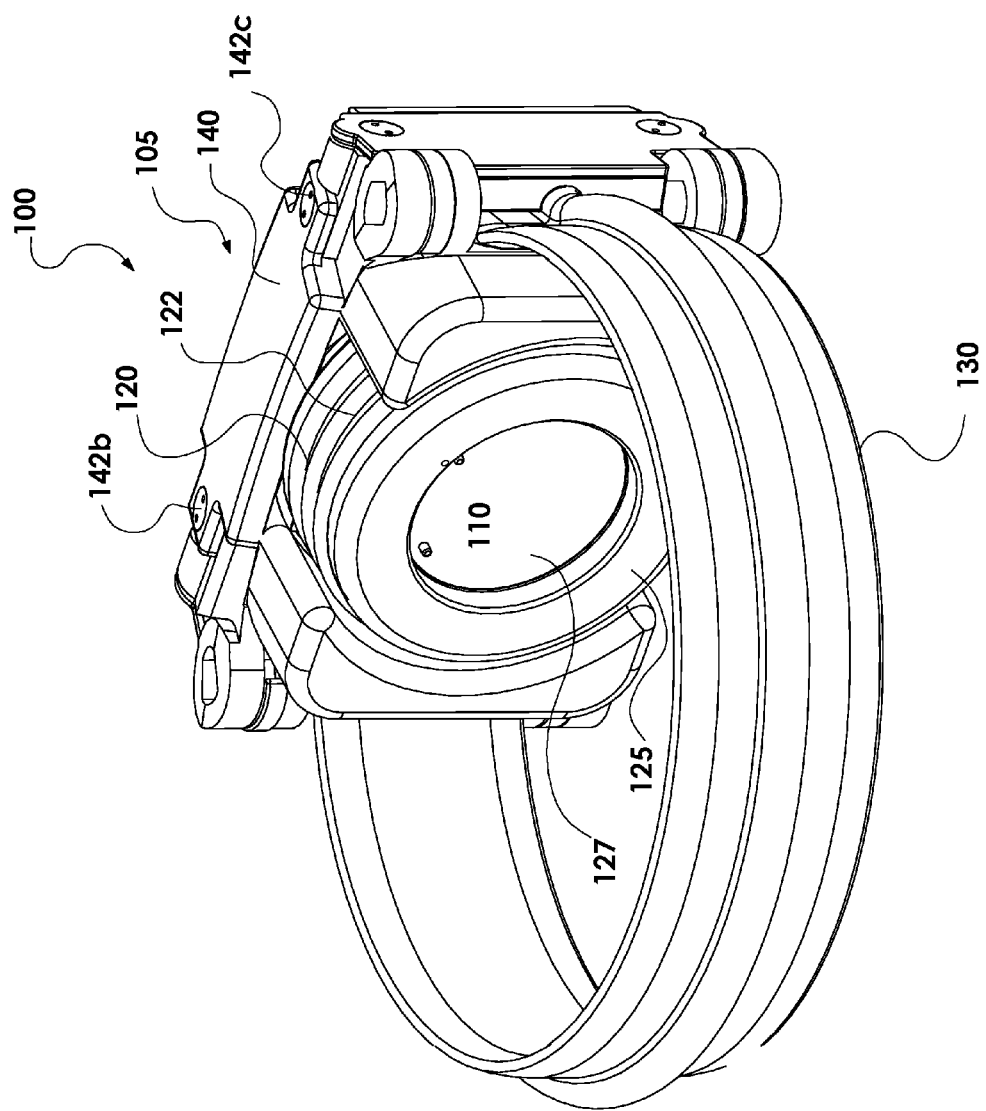
FIGS. 1a-1d depict an alcohol monitoring device in accordance with various embodiments of the present invention.

Turning to FIG. 1a, an alcohol monitoring device 100 is depicted in accordance with various embodiments of the present invention. Alcohol monitoring device 100 includes a body 105 that includes various monitoring and/or tracking circuitry. Such circuitry may include, but is not limited to, alcohol detection circuitry, location circuitry and/or tamper circuitry. The alcohol detection circuitry may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. In addition, the monitoring circuitry may include transmission and/ore reception circuitry as is known in the art for transmitting information from alcohol monitoring device 100, and receiving information at alcohol monitoring device 100. The information transmitted by alcohol monitoring device may include an indication of whether a monitored individual has been consuming alcohol and to what level the consumption has progressed. The information may be transmitted to a central monitoring station where it is monitored. Based on the disclosure provided herein, one of ordinary skill in the art will recognize a variety of information that may be transmitted to/from alcohol monitoring device, a variety of uses of such information, and a variety of transmission methods and protocols that may be utilized in accordance with different embodiments of the present invention. The tamper circuitry may include any circuitry known in the art that are capable of determining whether any interference with alcohol monitoring device 100. Such interference may include, but is not limited to, blocking the alcohol sensor, interfering with the transmission of information to/from alcohol monitoring device 100, and/or cutting an attachment securing alcohol monitoring device 100 to the human subject. Such tamper sensors may include, but are not limited to, a proximity sensor that is able to determine whether alcohol monitoring device 100 is within reasonable proximity of the skin of the monitored individual. Based on the disclosure provided herein, one of ordinary skill in the art will recognize a variety of tamper sensors that may be used in conjunction with the various embodiments of the present invention. The various sensors included in alcohol measurement device 100 may include, but are not limited to, blockage sensor indicating that no gas is being allowed to reach an included alcohol sensor, a temperature sensor, a proximity sensor indicating that alcohol measurement device is within a defined range of the monitored individual, a skin probe capable of measuring skin resistance as an indication of whether alcohol measurement device is still being worn by the monitored individual, and/or the like. Based on the disclosure provided herein, one of ordinary skill in the art will recognize a variety of other sensors that may be used in relation to different embodiments of the present invention.

Body 105 is attachable to a human subject using a strap 130. Strap 130 is attachable using some sort of buckle or other connector as are known in the art. In some cases, strap 130 includes a continuity detector (not shown) imbedded therein. In one particular embodiment of the present invention, the continuity detector is an electrical conductor extending around strap 130 and making a connection in body 105. As such, when strap 130 is either unbuckled or cut, the electrical conductor is broken and the break is detected by circuitry within body 105. In other particular embodiments of the present invention, the continuity detector is a fiber optic conductor that may similarly be used to determine whether strap 130 has been unbuckled or cut. Based on the disclosure provided herein, one of ordinary skill in the art will appreciate a variety of straps and associated securing devices that may be used in accordance with different embodiments of the present invention to secure body 105 to a monitored individual. In one particular embodiment, strap 130 includes an outer case with an imbedded fiber optic continuity conductor and banding for added strength.

Body 105 includes an alcohol sensor 110 that is maintained at a controlled distance from the monitored individual's skin by a dermal seal 125 and a telescoping housing 120. The combination of dermal seal 125 and telescoping housing 120 create a reasonably stable gas region 127 between alcohol sensor 110 and the monitored individual's skin. Dermal seal 125 may be, for example, a set of foam pads that are capable of creating a reasonable seal with the skin of a monitored individual, and yet are comfortable to the monitored individual. In particular instances, the foam pads are made of closed cell foam that allows for positioning and ergonomic fit. Based on the disclosure provided herein, one of ordinary skill in the art will recognize other materials that may be used to form dermal seal 125 in accordance with the various embodiments of the present invention. Telescoping housing 120 is operable to press alcohol sensor 110 near the skin of the monitored individual. Because of this, alcohol sensor 110 is maintained at a reasonably constant distance from the monitored individual's skin even when the individual is moving. This promotes better readings from alcohol sensor 110 without the need to tighten strap 130 beyond a comfortable point. As more fully described below, in one embodiment of the present invention, telescoping housing 120 includes an expandable bellows 122 that allows for movement of alcohol sensor 110 relative to body 105, and a spring (not shown) that presses alcohol sensor 110 and dermal seal 125 away from body 105 and toward the human subject's skin. In particular instances of the aforementioned embodiments, expandable bellows 122 is made of rubber, while in other instances it is formed of some type of flexible plastic. Based on the disclosure provided herein, one of ordinary skill in the art will recognize a variety of materials that may be used to create expandable bellows 122 in accordance with various embodiments of the present invention.

Body 105 also includes a water tight compartment 140 that includes a replaceable liquid cartridge (not shown) and electronics (not shown) for operating alcohol monitoring device 100. Water tight compartment 140 is accessible by removing temper resistant screws 142. In some embodiments of the present invention, tamper resistant screws 142 may require a special tool for removal to minimize the possibility that a monitored individual will open water tight compartment 140 and attempt to interfere or otherwise control the operation of alcohol monitoring device 100. In other embodiments of the present invention, tamper resistant screws 142 are only one way devices allowing for the closure of water tight compartment 140. Opening water tight compartment 140 requires the destruction of tamper resistant screws 142. When water tight compartment 140 is to be resealed, a new pair of tamper resistant screws is required.

In this way, any unauthorized opening of water tight compartment 140 will be readily apparent. In some cases, the aforementioned approach may be combined with a sensor (not shown) that indicates that water tight compartment 140 is open. Thus, when water tight compartment 140 is opened an error message may be prepared and transmitted to a central monitoring location by alcohol monitoring device 100. This would allow for detection of any tampering within a reasonable period of when the tampering occurred, and additional scrutiny of the monitored individuals behavior during that period.

Figure 1B:
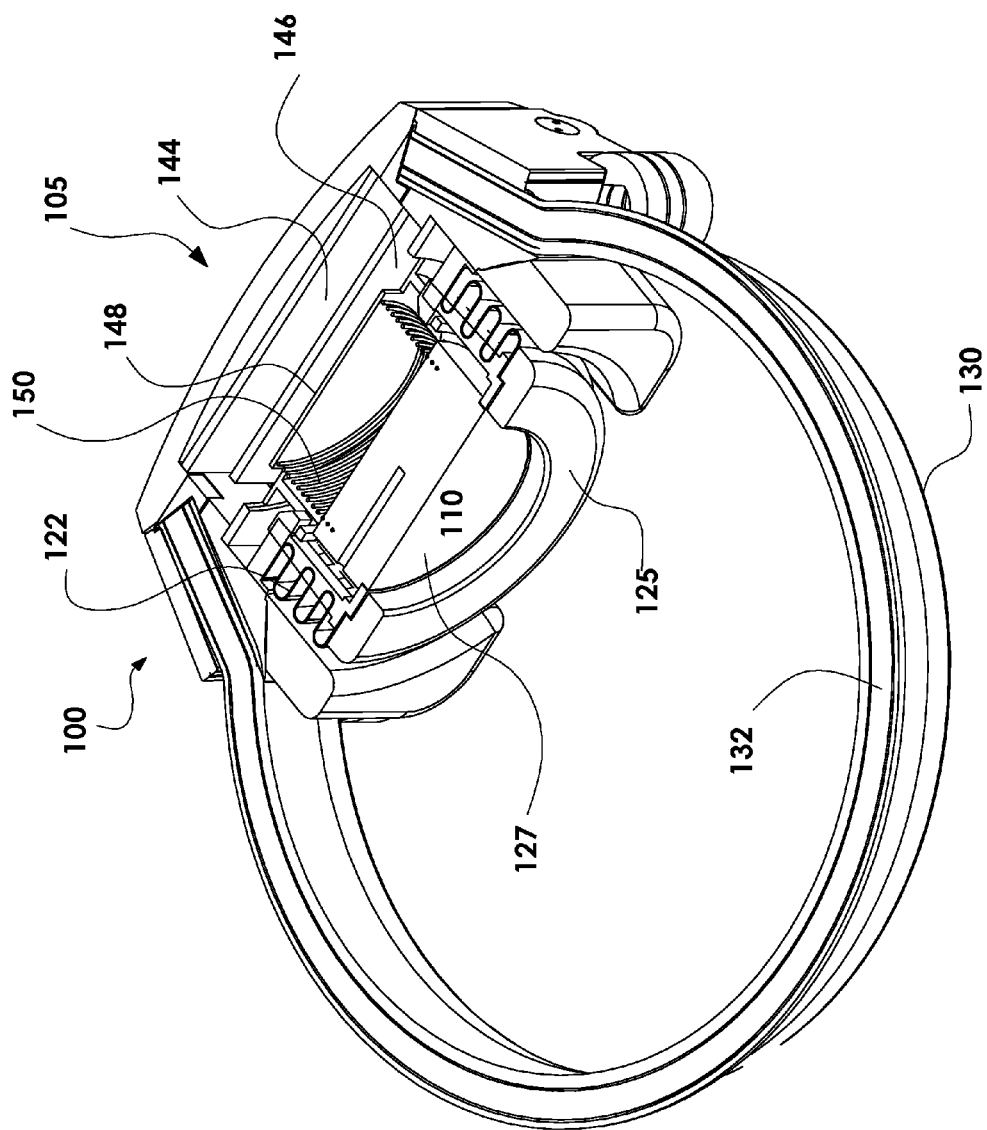

Turning to FIG. 1b, a cut away view of alcohol monitoring device 100 is presented. Of interest, expandable bellows 122 are shown as having a serpentine shape that allows for extension away from and toward body 105. Also shown is a spring 150 that provides the force for moving alcohol sensor 110 toward the skin of the monitored individual. In addition, a fiber optic conductor 132 is shown extending through strap 130. The interior of water tight compartment 140 is shown with an area 144 to hold a replaceable liquid cartridge (not shown), and an area 146 for electronic circuitry (not shown) for controlling the various operations of alcohol monitoring device 100. A bulk head 148 provides an area for spring 150 to press against and forms the outer wall of water tight compartment 140.

Figure 1C:
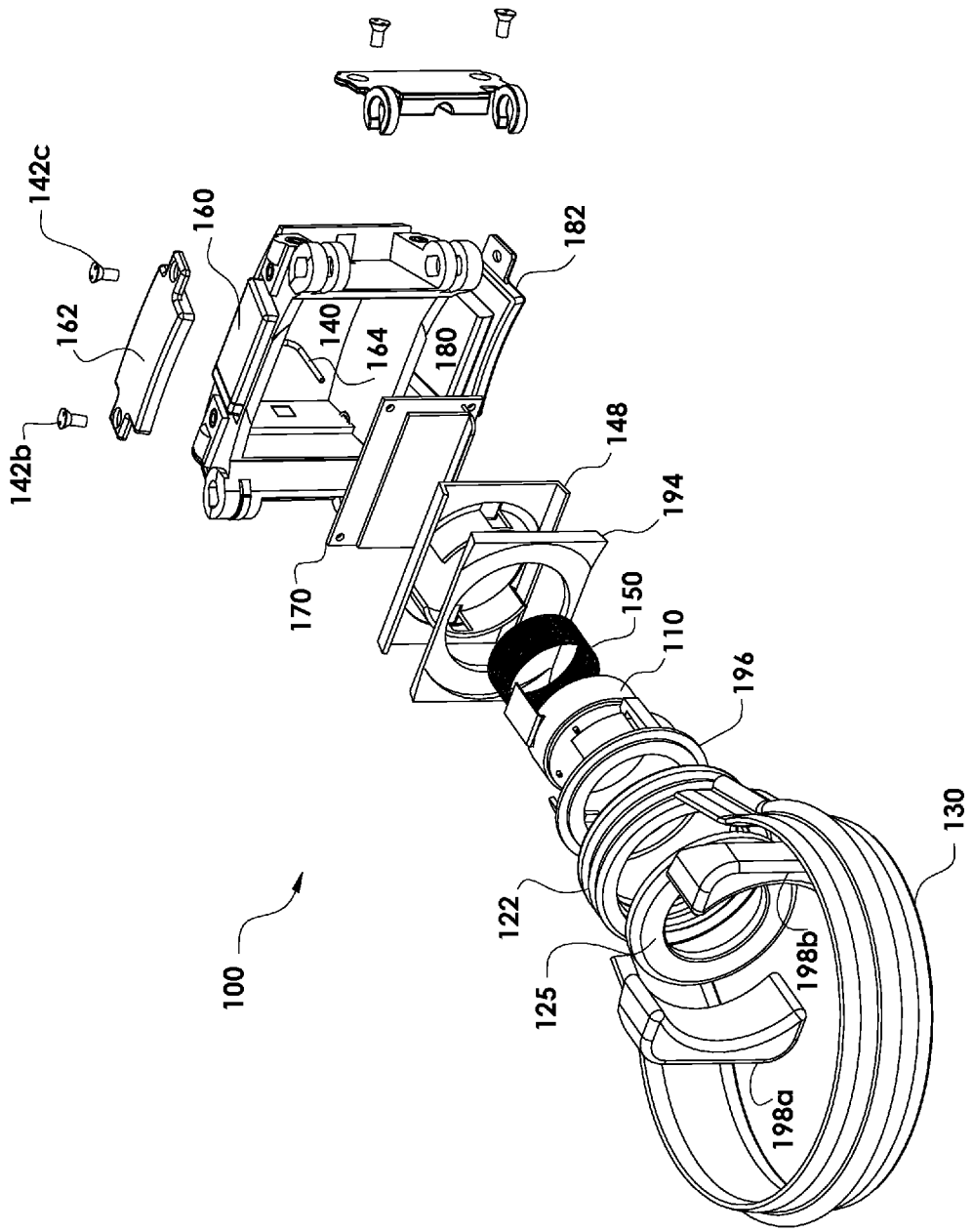

Turning to FIG. 1c, an exploded view of alcohol monitoring device 100 is presented. As shown, a battery 180 is connected to body 105 using a removable connector plate 182. Battery 180 provides power to operate alcohol monitoring device 100. A replaceable liquid cartridge 160 is placed in water tight compartment 140 and held in place by an outer plate 162 that is held in place by tamper resistant screws 142. In one embodiment of the present invention, liquid cartridge 160 is a plastic container that includes a supply of water used to operate alcohol sensor 110. Use of such a liquid cartridge allows for easy replenishment of water. In some cases, the water is distilled water that is not always readily available in the field. By using such a replaceable liquid cartridge, quick and easy replenishment of any desired liquid is rendered more manageable. A feed line 164 allows for dispersing liquid from liquid cartridge 160 to alcohol sensor 110. In some cases, feed line 164 is implemented as a wick capable of transporting a defined saturation of liquid.

An electronic circuit board 170 holds electronics responsible for controlling the various operations of alcohol monitoring device 100, and is connected in water tight compartment 140. A case cover 194 and bulk head 148 separates water tight compartment 140 from alcohol sensor 110. Spring 150 presses alcohol sensor 110 away from body 105 and toward the skin of the monitored individual. A sensor carriage 196 captures alcohol sensor 110 and allows it to move in and out and stay within a desired range of the monitor individual's skin. Expandable bellows 122 contact dermal seal 125 that includes foam pads 198 on opposite sides.

Figure 1D:
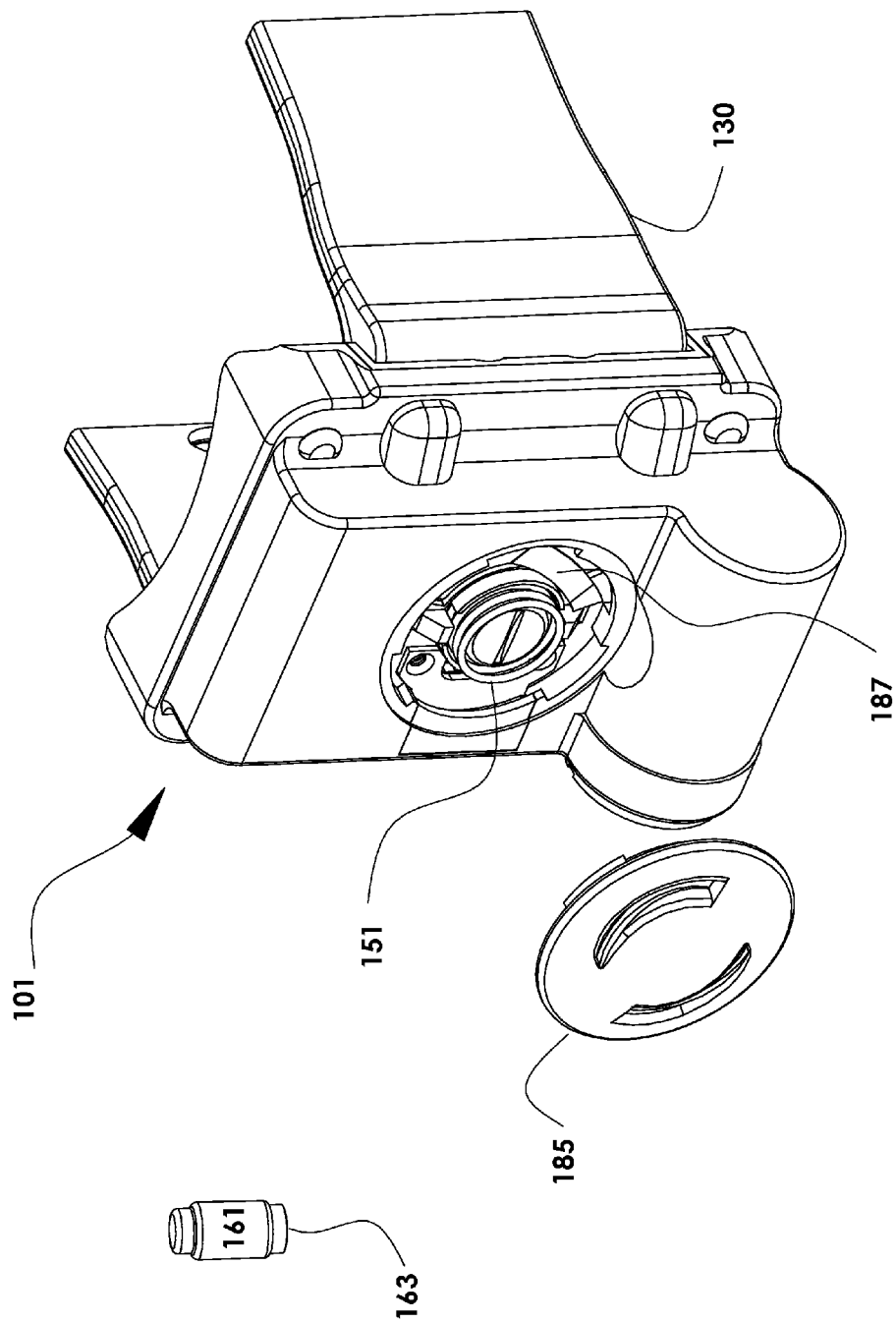

Turning to FIG. 1d, an alternative embodiment of a body 101 that may be used in place of body 105 is depicted. As shown, body 101 includes an opening in which a spring 151 is placed. Spring 151 is used similar to spring 150 to press an alcohol sensor (not shown) away from body 101 and toward the skin of the monitored individual. A cylindrical liquid cartridge 161 may be placed inside of spring 151. One end of cylindrical cartridge 161 includes a wick that assures a defined range of moisture saturation in proximity of the alcohol sensor. Cylindrical cartridge 161 is designed to be replaceable in the field. In one embodiment of the present invention, cylindrical cartridge 161 is a plastic container that includes a supply of water used to operate alcohol sensor 110. Use of such a replaceable cartridge allows for easy replenishment of water. In some cases, the water is distilled water that is not always readily available in the field. By using such a replaceable liquid cartridge, quick and easy replenishment of any desired liquid is rendered more manageable.

Spring 150 and cylindrical cartridge 161 are held in place by tamper resistant cap 185. Tamper resistant cap 185 is installed by placing it onto body 101 over spring 150 and cylindrical cartridge 161 and turned a quarter turn. When initially pressed onto body 101, tamper resistant cap 185 causes a flat spring 187 to press inward. Upon turning tamper resistant cap 185, it locks into body 101 with flat spring 187 extending away from body 101 into a void on tamper resistant cap 185. In the extended condition, flat spring 187 precludes twisting tamper resistant cap 185 to open body 101. Thus, the only way to access cylindrical cartridge 161 is to break tamper resistant cap 185. Thus, any unauthorized access to body 101 will be readily apparent. When replacing cylindrical cartridge 161 with a full cartridge, tamper resistant cap 185 is broken and a new cylindrical cartridge 161 is inserted in place of the replaced cartridge. A new tamper resistant cap 185 is then installed.

Figure 2A:
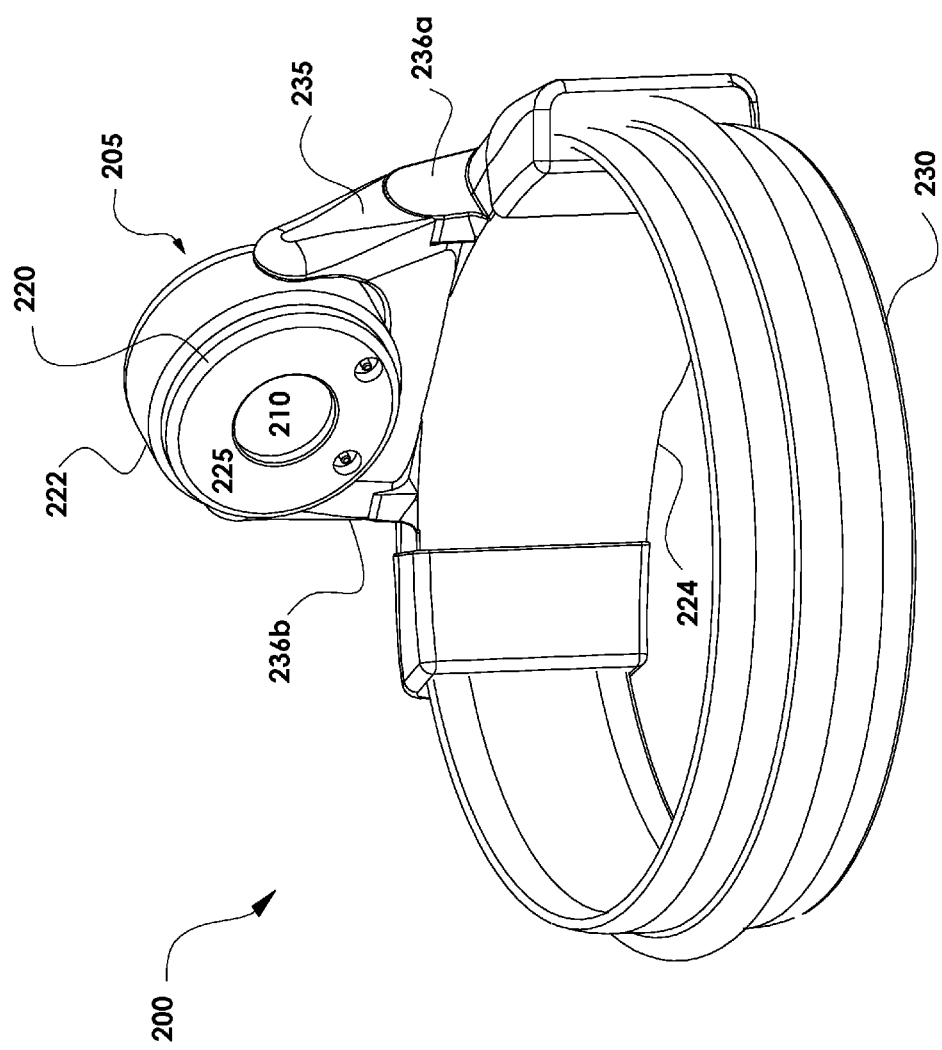
FIGS. 2a-2c depict another alcohol monitoring device in accordance with different embodiments of the present invention.

Turning to FIG. 2a, an alcohol monitoring device 200 is depicted in accordance with various embodiments of the present invention. Alcohol monitoring device 200 includes a body 205 that includes various monitoring and/or tracking circuitry. Such circuitry may include, but is not limited to, alcohol detection circuitry, location circuitry and/or tamper circuitry. The alcohol detection circuitry may include a fuel cell based on PEM sensor technology available from Giner Inc. of Newton, Mass., or any other alcohol detection sensor known in the art. The monitoring circuitry may include location monitoring circuitry as is known in the art, or other monitoring circuitry used to determine attributes and/or location of a monitored individual. In addition, the monitoring circuitry may include transmission and/ore reception circuitry as is known in the art for transmitting information from alcohol monitoring device 200, and receiving information at alcohol monitoring device 200. The tamper circuitry may include any circuitry known in the art that are capable of determining whether any interference with alcohol monitoring device 200.

Body 205 is attachable to a human subject using a strap 230. Strap 230 is attachable using some sort of buckle or other connector as are known in the art. In some cases, strap 230 includes a continuity detector (e.g., either an electrical conductor or optical conductor) imbedded therein. As such, when strap 230 is either unbuckled or cut, the conductor is broken and the break is detected by circuitry within body 205. In one particular embodiment, strap 230 includes an outer case with an imbedded fiber optic continuity conductor and banding for added strength.

Body 205 includes an alcohol sensor body 222 and an electronics body 224. Electronics body 224 houses a battery and electronic circuitry responsible for the various operations of alcohol monitoring device 200. Alcohol sensor body 222 holds a sensor housing 225 that articulates to stay in contact with the skin of a monitored individual. In some cases, alcohol sensor body 222 may include a spring and an expandable bellows similar to that discussed above in relation to alcohol monitoring device 100. Alcohol sensor body 222 operates to hold an alcohol sensor 210 within a defined range of the skin of a monitored individual. This assures that more accurate readings are possible.

Alcohol sensor body 222 is held in relation to electronics body 224 by a support bracket 235 connected via torsion hinges 236 on either side. Torsion hinges 236 operate to force alcohol sensor body 222 toward the center of strap 230, thus causing alcohol sensor 210 to be disposed nearer the skin of the monitored individual. In one particular embodiment of the present invention, torsion hinges 236 are spring loaded hinges providing only a minimal amount of pressure sufficient to keep sensor body 222 in contact the appropriate skin.

Figure 2C:
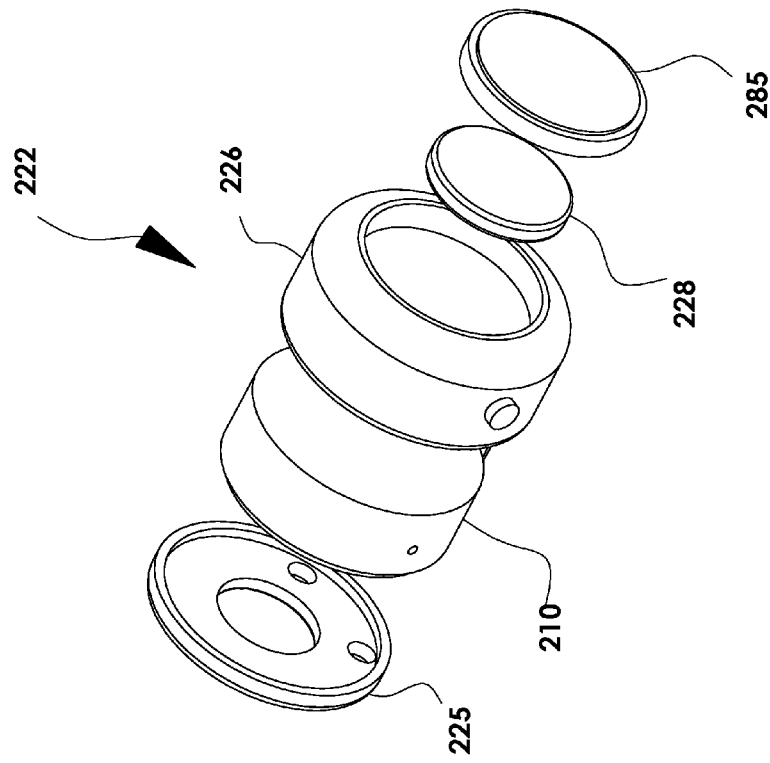
Figure 2B:
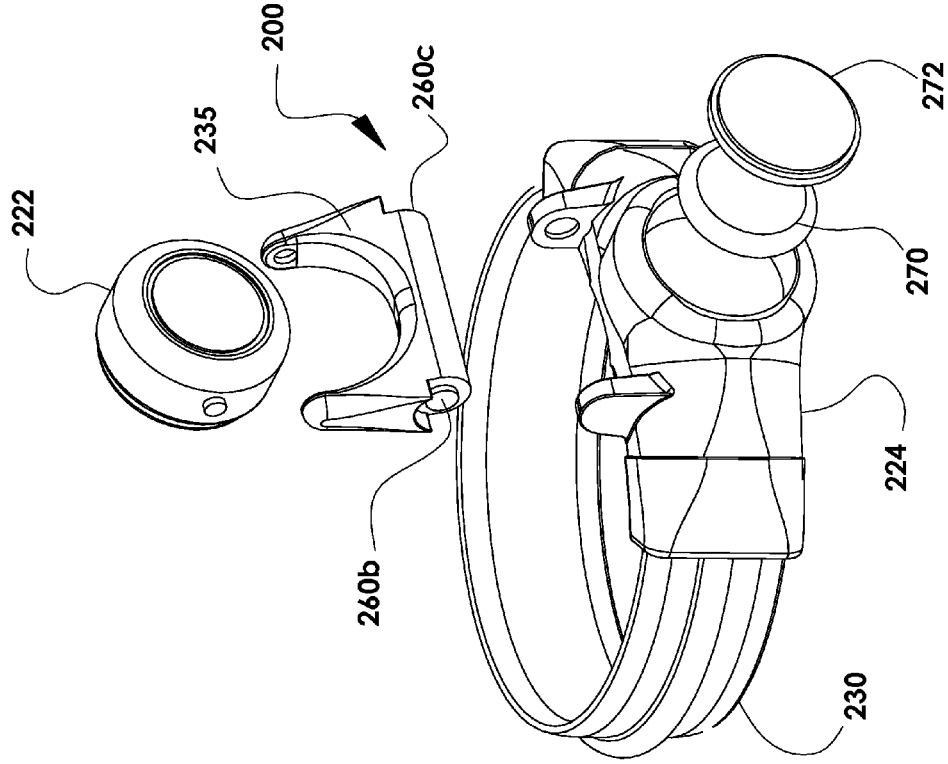

Turning to FIG. 2b, an exploded view of alcohol monitoring device 200 is provided. In particular, support bracket 235 including torsion hinges 236 is shown disconnected from both alcohol sensor body 222 and electronics body 224. In addition, a tamper resistant cap 272 is removed from electronics body 224 revealing a battery 270. Tamper resistant cap 272 is installed by placing it onto electronics body 224 over battery 270 and turned a quarter turn. Tamper resistant cap 272 may be installed over a flat spring similar to that discussed above in relation to tamper resistant cap 185. Such an approach requires damaging tamper resistant cap 272 whenever it is removed rendering any tampering evident. Alternatively, or in addition, tamper resistant cap 272 may require a specialized tool for removal to minimize the possibility that a monitored individual will tamper with alcohol monitoring device 200. Further, in some cases, the aforementioned approaches may be combined with a sensor (not shown) that indicates that tamper resistant cap 272 has been removed. Thus, when tamper resistant cap 272 is removed, an error message may be prepared and transmitted to a central monitoring location by alcohol monitoring device 200. This would allow for detection of any tampering within a reasonable period of when the tampering occurred, and additional scrutiny of the monitored individuals behavior during that period.

Turning to FIG. 2c, an exploded view of alcohol sensor body 222 is shown. In this embodiment, alcohol sensor body 222 includes an outer casing 226 into which alcohol sensor 210 is placed and secured therein using a face plate 225 that doubles as a dermal seal. In some cases, dermal seal 225 is made of a plastic material sturdy enough to maintain alcohol sensor 210 in place and pliable enough when placed in relation to human skin to render a reasonable seal. Based on the disclosure provided herein, one of ordinary skill in the art will recognize a variety of materials that may be used to create dermal seal 225 in accordance with different embodiments of the present invention.

Outer casing 226 additionally houses a replaceable liquid cartridge 228 that is maintained in place by a tamper resistant cap 285. A wick or liquid feed mechanism traverses an inner wall 228 of outer casing to allow liquid from liquid cartridge 228 to reach alcohol sensor 210. In one embodiment of the present invention, replaceable liquid cartridge 228 is a plastic container that includes a supply of water used to operate alcohol sensor 210. Use of such a liquid cartridge allows for easy replenishment of water. In some cases, the water is distilled water that is not always readily available in the field. By using such a replaceable liquid cartridge, quick and easy replenishment of any desired liquid is rendered more manageable.

Tamper resistant cap 285 is installed by placing it onto outer casing 226 over liquid cartridge 228 and turned a quarter turn. Tamper resistant cap 285 may be installed over a flat spring similar to that discussed above in relation to tamper resistant cap 185. Such an approach requires damaging tamper resistant cap 285 whenever it is removed rendering any tampering evident. Alternatively, or in addition, tamper resistant cap 285 may require a specialized tool for removal to minimize the possibility that a monitored individual will tamper with alcohol monitoring device 200. Further, in some cases, the aforementioned approaches may be combined with a sensor (not shown) that indicates that tamper resistant cap 285 has been removed. Thus, when tamper resistant cap 285 is removed, an error message may be prepared and transmitted to a central monitoring location by alcohol monitoring device 200. This would allow for detection of any tampering within a reasonable period of when the tampering occurred, and additional scrutiny of the monitored individuals behavior during that period.

Figure 3B:
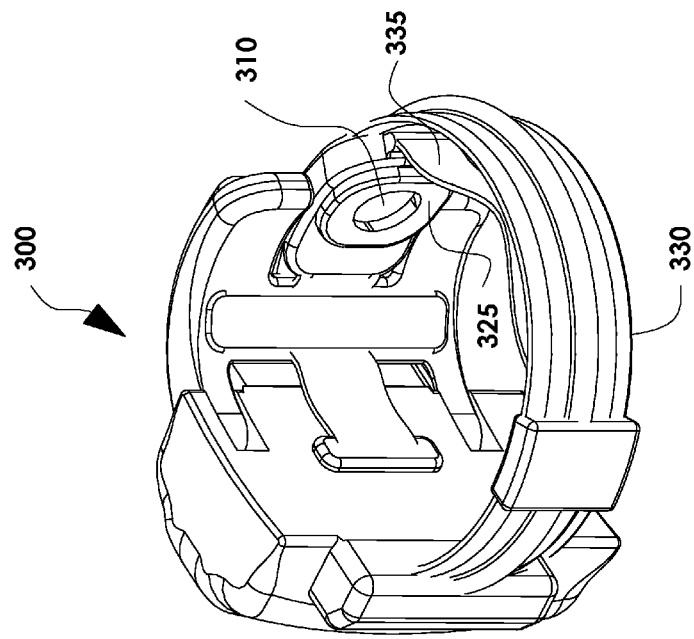
FIGS. 3a-3b depict yet another alcohol monitoring device in accordance with yet other embodiments of the present invention.
Figure 3A:
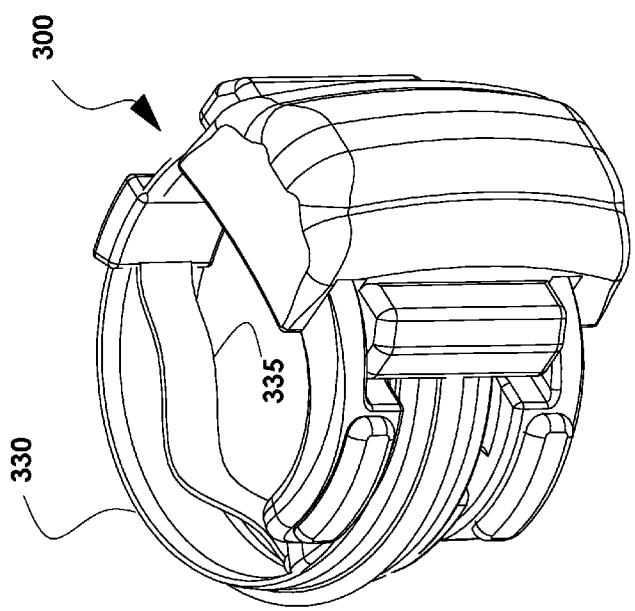

Turning to FIGS. 3a-3b, two views of another alcohol monitoring device 300 is depicted in accordance with yet other embodiments of the present invention. As shown, alcohol monitoring device 300 includes an alcohol sensor 310 that is maintained a desired distance from the skin of a monitored individual by a dermal seal 325. Alcohol sensor 310 is maintained in proximity to the skin though use of a flexible sub-strap 335 that is more flexible than a main strap 330. Flexible sub-strap 335 is attached to a sensor assembly including alcohol sensor 310 and dermal seal 325. This allows alcohol sensor 310 to be maintained near the skin of the monitored individual without requiring that the entire alcohol monitoring device 300 be maintained in the same proximity. This allows for greater comfort and improved alcohol measurement results.

Figure 4:
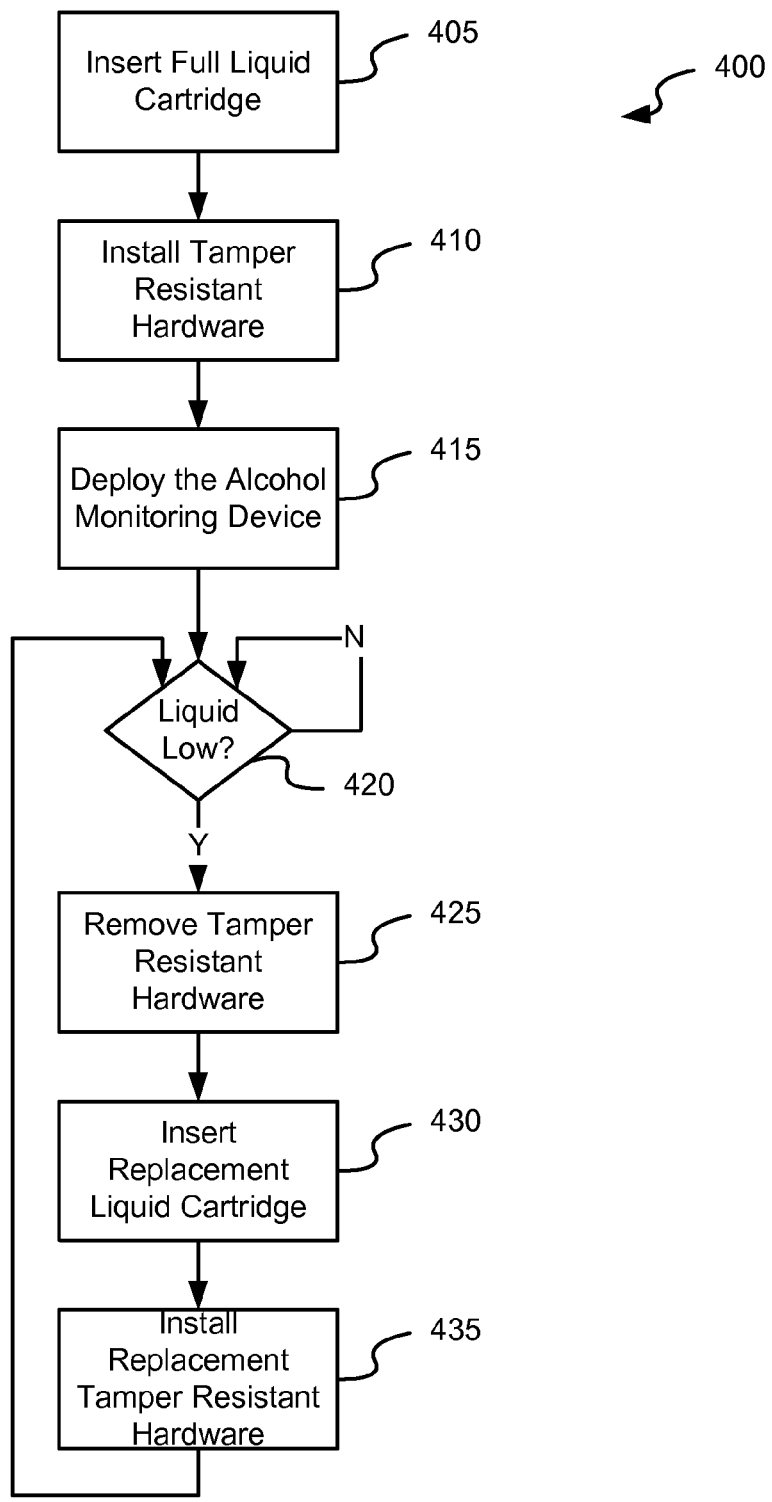
FIG. 4 is a flow diagram depicting a process for servicing an alcohol monitoring device in accordance with some embodiments of the present invention.

Turning to FIG. 4, a flow diagram 400 depicts a process for servicing an alcohol monitoring device in accordance with some embodiments of the present invention. Following flow diagram 400, a full liquid cartridge is initially installed in an alcohol measuring device (block 405). This process may include, for example, inserting a new liquid cartridge into an opening of the alcohol monitoring device designed to hold the cartridge. Such a liquid cartridge may include, for example, a supply of distilled, de-ionized water that is designed to support operation of the alcohol monitoring device for a desired range of time. Inclusion of a larger cartridge allows for greater extension of device operation between maintenance intervals.

Once the liquid cartridge is installed (block 405), tamper resistant hardware is installed over the liquid cartridge to hold it in place (block 410). This may include, but is not limited to, installing a plate using tamper resistant screws or covering the opening through which the liquid cartridge is inserted using a tamper resistant cap. Further, it may include turning on a sensor that indicates that a tamper has occurred if such circuitry is available. The alcohol monitoring device may then be deployed (block 415). This may include securing the alcohol measuring device to a monitored individual.

During deployment, it may be determined whether the liquid in the installed liquid cartridge is low (block 420). This may include, for example, determining that the installed liquid sensor has been in for a certain time period and that it needs to be replaced. In other cases, the alcohol monitoring device may be able to detect when the liquid in the liquid cartridge is low. In such a case, a sensor message may be transmitted to a central monitoring system. In either case, where it is determined that the liquid level is potentially or actually low, the alcohol monitoring device is serviced. Such service may include summoning the monitored individual to a prescribed location where the device is serviced. This may be a scheduled service time corresponding, for example, to a visit with a parole officer. Alternatively, a technician or parole officer may visit the monitored individual and service the alcohol monitoring device in situ. Use of a cartridge based approach to the liquid reservoir makes such servicing possible.

The servicing includes removing the tamper resistant hardware holding the liquid cartridge in place (block 425). This may include destroying part of the hardware which will need to be replaced with new parts. A new liquid cartridge is then inserted in place of the removed liquid cartridge rendered accessible by removing the tamper resistant hardware (block 430), and replacement tamper resistant hardware is installed to hold the replacement liquid cartridge in place (block 435).

Figure 5:
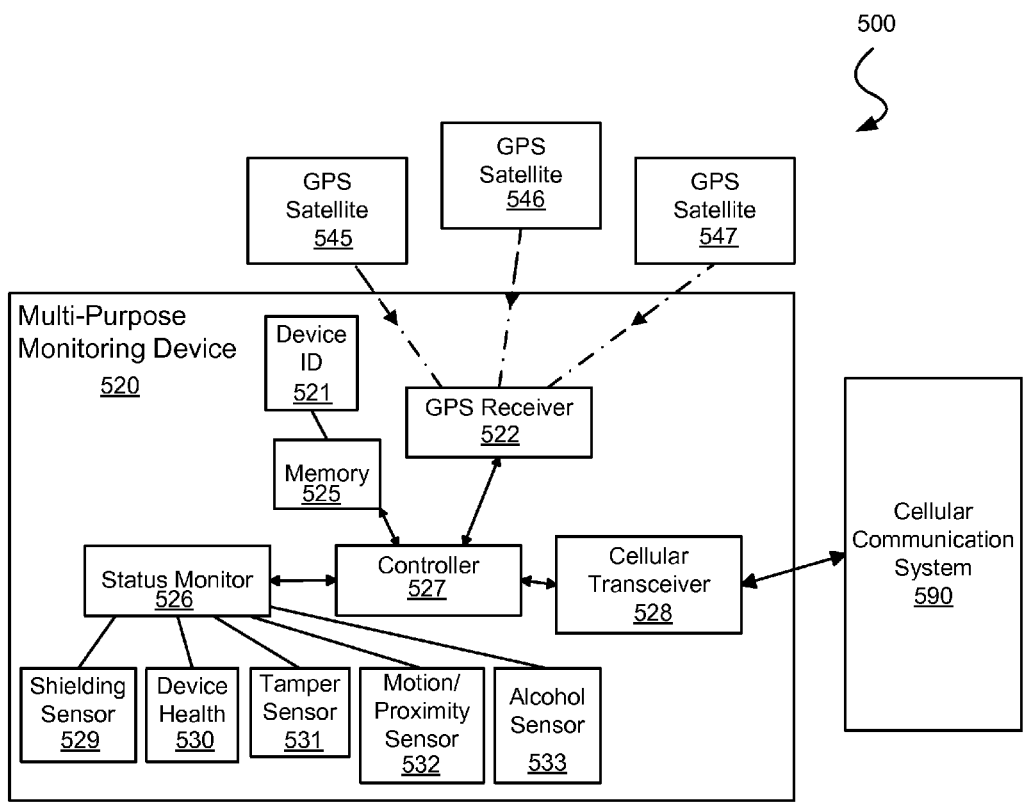
FIG. 5 depicts the block diagram of a monitoring device capable of monitoring subject location as well as alcohol usage.

Turning to FIG. 5, a tracking and alcohol monitoring system 500 is depicted in accordance with some embodiments of the present invention. Tracking and monitoring system 500 includes a multi-purpose monitoring device 520 that is capable of both tracking an individual and monitoring alcohol consumption of the individual. This device can be incorporated in the electronics of the devices of FIGS. 1, 2 and 3. As shown, multi-purpose monitoring device 520 includes a GPS receiver 522 that is capable of receiving GPS information from GPS satellites 345, 346, and 347 respectively. GPS receiver 322 is useful for determining physical locations, i.e. whenever GPS receiver 322 is powered-on, and also as long as receiving sufficient GPS satellites signal transmissions.

Multi-purpose monitoring device 520 includes a device ID 521 that may be maintained in a memory 525, and thus is accessible by a controller 527. Controller 57 is able to interact with GPS receiver 522 and memory 525 at times for storing and generating records of successively determined GPS locations. Controller 527 may be, but is not limited to, a microprocessor, microcontroller or other device known in the art that is capable of executing software or firmware instructions. Memory 525 may be any type of memory known in the art such as, for example, a EEPROM or RAM memory. Instructions executable by controller 527 may be maintained in memory 525.

Controller 527 of subject device 520 at times functions in conjunction with a cellular transceiver 528 to send and receive data and signals through cellular communication system 590. This link at times is useful for passing information and/or control signals between a central monitoring system (not shown) and multi-purpose monitoring device 520. The information transmitted may include, but is not limited to, location information, alcohol information, and information about the status of multi-purpose monitoring device 520. Based on the disclosure provided herein, one of ordinary skill in the art will recognize a variety of information that may be transferred via cellular communication system 590.

Various embodiments of multi-purpose monitoring device 520 include a variety of sensors capable of determining the status of multi-purpose monitoring device 520, and of the individual associated therewith. For example, a status monitor 526 may include one or more of the following subcomponents: a set of shielding sensors 529 that are capable of determining whether subject device is being shielded from receiving GPS signals and/or if GPS jamming is ongoing, a set of device health indicators 530, a tamper sensor 531 capable of determining whether unauthorized access to subject device 520 has occurred or whether subject device 520 has been removed from an associated human subject, a motion/proximity sensor 532 capable of determining whether subject device 520 is moving and/or whether it is within proximity of an individual associated with multi-purpose monitoring device 520, and/or an alcohol sensor 533 such as that described herein. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into subject device 520 according to various different instances and/or embodiments of the present invention. In some cases, transmission of alcohol data is done at one frequency, and house arrest information is transmitted at another frequency. In one particular embodiment of the present invention, house arrest information (i.e., location information) is transmitted using a 300 MHz-320 MHz, and alcohol information is transmitted using a 902 MHz-928 MHZ band. The higher frequency band allows for transmission of substantial amounts of information, while the lower frequency band allows for transmission of smaller amounts of data.

Figure 6:
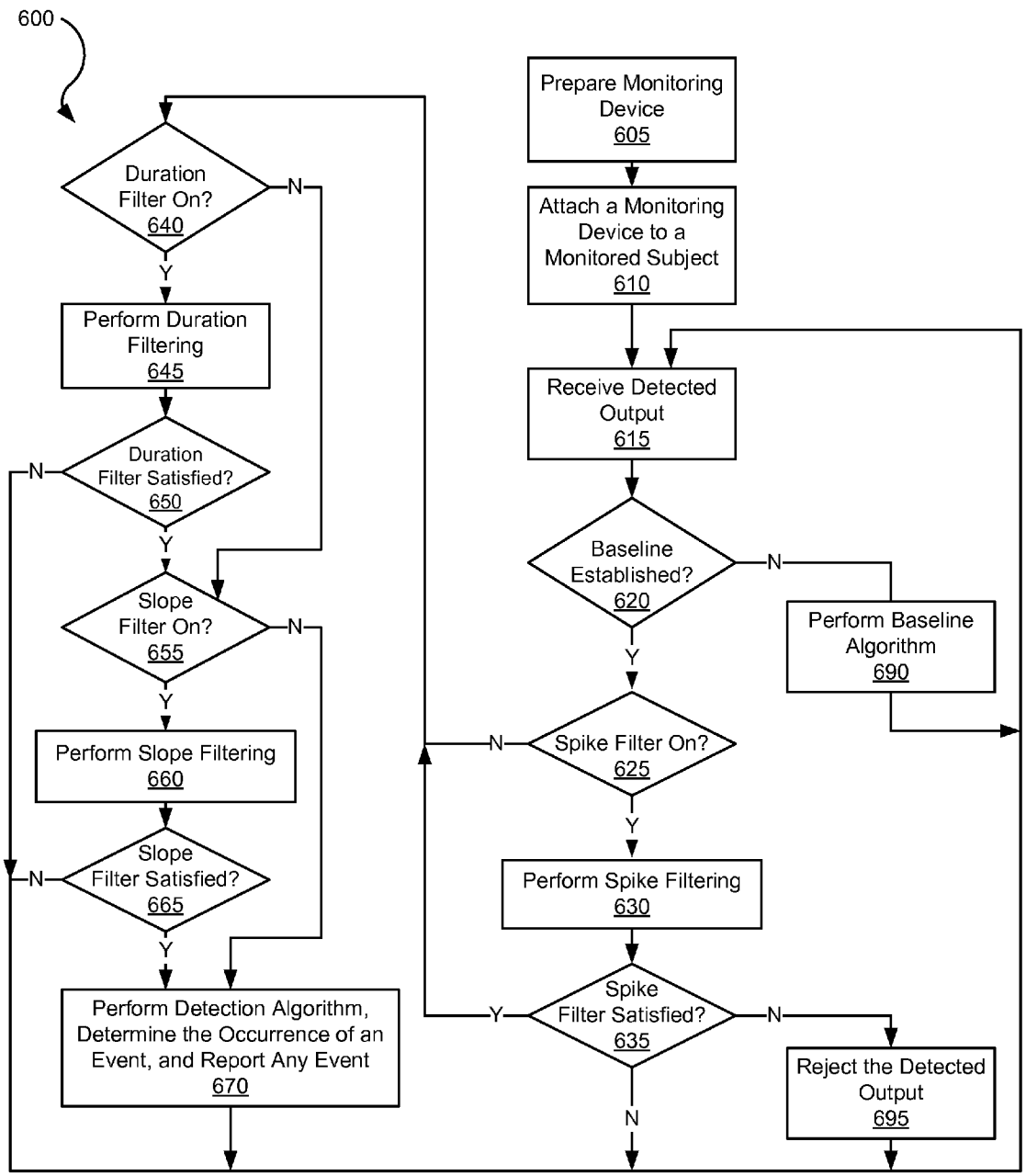
FIG. 6 is a flow diagram depicting a method in accordance with some embodiments of the present invention for detecting and reporting secretions.

Turning to FIG. 6, a flow diagram 600 depicts a method in accordance with some embodiments of the present invention for detecting and reporting secretions. In some cases, the process of flow diagram 600 is implemented as computer executable instructions. Such computer executable instructions may be maintained in a memory that is communicably coupled to a processor. The processor may access and execute the instructions. Following flow diagram 600, a monitoring device is prepared (block 605). Such preparation may include, but is not limited to, configuring any configurable elements of the monitoring device, assuring proper operation of the monitoring device, and//or the like. Where, for example, the monitoring device may be alcohol monitoring device 100 described above, or another monitoring device capable of detecting one or more chemicals secreted transdermally. In addition, the monitoring device is attached to a monitored subject (block 610). This may include, for example, strapping a monitoring device around the leg of a human subject in such a way that it is difficult to remove, and if removed it provides some indication that tampering has occurred. Based upon the disclosure provided herein, one of ordinary skill in the art will recognize a variety of approaches and equipment that may be used to attach the monitoring device to a monitored subject.

Figure 7:
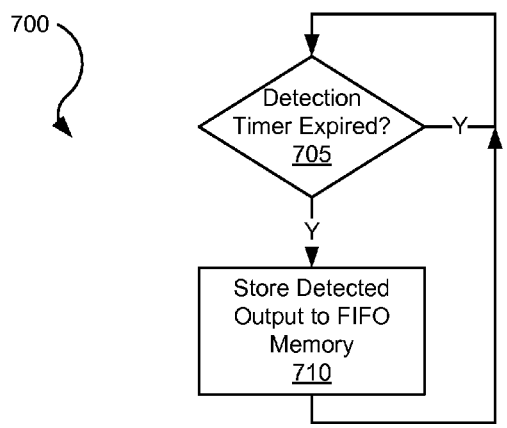
FIG. 7 is a flow diagram depicting a process for updating detected outputs in accordance with various embodiments of the present invention.

A sensor associated with the monitoring device senses transdermal chemical secretions from the monitored subject and provides an indication of the transdermal chemical secretions as a detected output to a processor of the monitoring device (block 615). One example of a process for updating detected outputs from the sensor is shown as flow diagram 700 of FIG. 7. Following flow diagram 700, it is determined whether a detector timer has expired (block 705). In one particular embodiment of the present invention, the detector timer expires and resets each five minutes. Based upon the disclosure provided herein, one of ordinary skill in the art will recognize other frequencies at which the detected output may be received from the sensor. Once the timer expires (block 705), the detected output is stored to a FIFO (First In—First Out) memory (block 710). The memory holds enough samples (i.e., instances of detected output sampled at periods over time) to run any detection algorithm and filtering employed. In one particular embodiment of the present invention, the memory holds twelve samples.

Returning to flow diagram 600, it is determined whether a baseline has been established (block 620). Where a baseline has not been established (block 620), a baseline algorithm is performed (block 690). The baseline algorithm establishes a baseline value for comparison with later detected outputs to determine whether a positive detection of a chemical secretion is identified. In some embodiments of the present invention, a calculated transdermal chemical concentration (TCC) is a linear value calculated using the following slope intercept equation:

$$y = mx + b,$$

where m represents slope and b is the y-intercept. In this case, the value of the slope is calculated in accordance with the following equation:

$$m = \frac{TCC_{max} - TCC_{min}}{Count_{max} - Count_{min}}.$$

Effectively, the baseline algorithm modifies the value of $Count_{min}$ for exam individual such that the slope and intercept is changed for each individual.

In particular, the baseline algorithm the standard deviation is calculated in accordance with the following equations:

$$S = \sqrt{\frac{\sum (x - \overline{X})^2}{n - 1}}, \text{ and}$$

$$S_{\overline{X}} = \frac{S}{\sqrt{n}}, \text{ and}$$

$$v = (n - 1)$$

where n is the number of samples utilized and v=the degrees of freedom. The value of $S_{\overline{x}}$ is used with the Student's t-distribution for the appropriate degrees of freedom to set a statistical probability bound around the arithmetic mean value $\overline{X}$. Depending upon the desired probability and the number of samples used to perform the baseline, an appropriate Critical Value (CV) of t is employed from standard statistical tables of the ordinates of the t distribution for degrees of freedom v. Where, for example, a 95% confidence level (probability α=1.0−0.95=0.05 in the two-tailed t distribution) is desired, the value 2.571 is selected when the number of samples used is six and v=5. As another example, where a probability of 99.5% is desired, the value 4.773 is employed with the same sample size and degrees of freedom. An upper limit and lower limit are set in accordance with the following equations:

lower limit=$\overline{x}$−CV*$S_{\overline{x}}$; and upper limit=$\overline{x}$+CV*$S_{\overline{x}}$.

Thus, using the example of 95% confidence and six samples, the appropriate critical value is 2.571 yielding the following equations for the upper limit and the lower limit:

lower limit=$\overline{x}$−(2.571*$S_{\overline{x}}$) and upper limit=$\overline{x}$+(2.571*$S_{\overline{x}}$).

From this, a 95% statistical confidence interval or "difference limit" Δ limit is calculated as the simple difference between the upper limit and lower confidence limits. If Δ limit is less than a determined value (i.e., a limit set point), then it is determined that there is at least the corresponding probability that the true mean of the n samples has been found. Thus, for example, where the value 2.571 is used with the number of degrees of freedom being five a 95% probability is achieved where the difference (i.e., Δ limit) is less than the determined value. In this case, a baseline has been achieved and the baseline value is set to be the calculated arithmetic mean of the n samples.

Alternatively, where a baseline has been established (block 620), it is determined whether a spike filter is turned on (block 625). Where the spike filter is turned on (block 625), spike filtering is performed (block 630). The spike filter is used to eliminate spurious readings that may be identified by how far from an expected value they fall. In one particular embodiment of the present invention, the spike filter identifies a received detected output (i.e., $TCC_t$) as a spike where one or both of the following conditions is met: the immediately preceding detected output (i.e., $TCC_{t-1}$) is less greater than a defined value, and the received detected output (i.e., $TCC_t$) minus the immediately preceding detected output (i.e., $TCC_{t-1}$) is greater less than the defined value. Where the defined value is 0.02, the following pseudo-code describes the operation of the spike filter:

```
IF (TCC_{t-1} < 0.02 AND (TCC_t - TCC_{t-1}) > 0.02)
{
    Spike Filter Satisfied
}
ELSE
{
    Spike Filter Not Satisfied
}
```

Where the spike filter is not satisfied (block 635), the detected output (current TCC) is rejected (block 695) and the process returns to await reception of the next detected output (block 615). Alternatively, where either the spike filter is not turned on (block 625) or the spike filter is satisfied (block 635), it is determined whether a duration filter is turned on (block 640).

Where the duration filter is turned on (block 640), duration filtering is applied (block 645). The duration filter is used to assure that whatever positive chemical detection that has occurred continues for a period of time before it is identified as reliable and reported. Where, for example, the chemical being detected is alcohol, physiology assures that the period of active detection extends for a substantial period of time suggesting that a positive detection that lasts for only a short period may be a false positive and should not be reported. In one particular embodiment of the present invention, the duration filter is satisfied where the six preceding detected outputs (i.e., $TCC_{t-5}$, $TCC_{t-4}$, $TCC_{t-3}$, $TCC_{t-2}$, $TCC_{t-1}$, $TCC_t$) are all greater than a defined value. Where the defined value is 0.02, the following pseudo-code describes the operation of the duration filter:

```
IF (TCC_{t-5}>0.02 AND TCC_{t-4}>0.02 AND TCC_{t-3}>0.02 AND
    TCC_{t-2}>0.02 AND TCC_{t-1}>0.02 AND TCC_t>0.02)
{
    Duration Filter Satisfied
}
ELSE
{
    Duration Filter Not Satisfied
}
```

Where the duration filter is not satisfied (block 650), the process returns to await reception of the next detected output (block 615) without reporting an event. Alternatively, where either the duration filter is not turned on (block 640) or the duration filter is satisfied (block 650), it is determined whether a slope filter is turned on (block 655).

Where the duration filter is turned on (block 640), duration filtering is applied (block 645). The duration filter is used to assure that whatever positive chemical detection that has occurred continues for a period of time before it is identified as reliable and reported. Where, for example, the chemical being detected is alcohol, physiology assures that the period of active detection extends for a substantial period of time suggesting that a positive detection that lasts for only a short period may be a false positive and should not be reported. In one particular embodiment of the present invention, the duration filter is satisfied where the six preceding detected outputs (i.e., $TCC_{t-5}$, $TCC_{t-4}$, $TCC_{t-3}$, $TCC_{t-2}$, $TCC_{t-1}$, $TCC_t$) are all greater than a defined value. Where the defined value is 0.02, the following pseudo-code describes the operation of the duration filter:

```
IF (TCC_{t-5}>0.02 AND TCC_{t-4}>0.02 AND TCC_{t-3}>0.02 AND
    TCC_{t-2}>0.02 AND TCC_{t-1}>0.02 AND TCC_t>0.02)
{
    Duration Filter Satisfied
}
ELSE
{
    Duration Filter Not Satisfied
}
```

Where the duration filter is not satisfied (block 650), the process returns to await reception of the next detected output (block 615) without reporting an event. Alternatively, where either the duration filter is not turned on (block 640) or the duration filter is satisfied (block 650), it is determined whether a slope filter is turned on (block 655).

Where the slope filter is turned on (block 655), slope filtering is applied (block 660).

The slope filter is used to assure that reporting of a chemical detection is only done where the quantity of the detected chemical is increasing. Where, for example, the chemical being detected is alcohol, physiology assures that the period of active detection includes an up slope extending over a first period of substantial duration, and a down slope extending over a second period of substantial duration. Assuring both duration and an up slope avoids reporting of less significant events in favor of reporting only more significant events. In one particular embodiment of the present invention, the slope filter is satisfied where the preceding detected output (i.e., $TCC_{t-1}$) is less than the current detected output ($TCC_t$). The following pseudo-code describes the operation of the slope filter:

```
IF (TCC_{t-1}<TCC_t)
{
    Slope Filter Satisfied
}
ELSE
{
    Slope Filter Not Satisfied
}
```

Where the slope filter is not satisfied (block 665), the process returns to await reception of the next detected output (block 615) without reporting an event. Alternatively, where either the slope filter is not turned on (block 655) or the slope filter is satisfied (block 665), a detection algorithm is performed, the occurrence of an event is determined, and any event is reported (block 670). An example of performing a detection algorithm, determination of an event, and reporting is discussed below in relation to a flow diagram 800 of FIG. 8.

Figure 8:
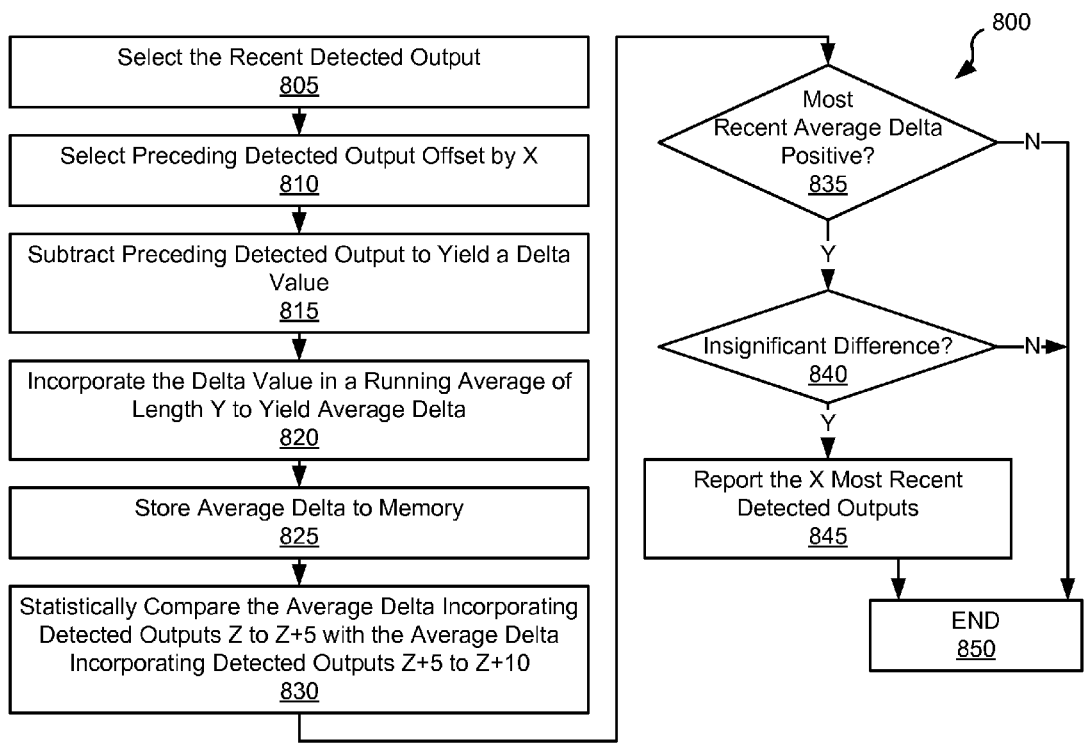
FIG. 8 is a flow diagram showing a method for determining and reporting a secretion in accordance with one or more embodiments of the present inventions.

Turning to FIG. 8, flow diagram 800 shows a method for determining and reporting a chemical event in accordance with one or more embodiments of the present inventions. Following flow diagram 800, the most recent detected output (i.e., $TCC_t$) is accessed from the memory where the detected outputs are stored (block 805), and the detected output offset by x (i.e., $TCC_{t-x}$) is accessed (block 810).). In some cases, the algorithm is a differenced moving average where the difference (i.e., x) equals six samples taken across successive equal time periods "t". The detected output offset by x (i.e., $TCC_{t-x}$) is subtracted from the most recent detected output (i.e., $TCC_t$) to yield a Delta Value in accordance with the following equation (block 815):

$$\text{Delta Value}=TCC_t-TCC_{t-x}.$$

The calculated Delta Values are then arithmetically averaged to form a moving average of sample size x to yield a Moving Average Delta (block 820). As an example, the moving average works on a fixed sample size that is moved across a larger set of samples.

At the conclusion of the first two x-period moving averages, a statistical comparison of the first x period moving average and the second x period moving average is performed (block 830). In some cases, the first x samples and the second x samples overlap by one point to ensure that single extreme values at the cusp of the two time series affect their independent statistical variances $S^2$ equally. This statistical comparison statistically evaluates the difference between the most recent x period moving average and the immediately preceding x period moving average. To do this, standard statistical tests may be employed such as, for example, a Student's 't'. In one particular case, the statistical tests are used to evaluate the null hypothesis ($H_O$) that the means are equivalent at a defined probability ($\alpha$). In one case, the defined probability is 99% (i.e., $\alpha=0.01$). In such a case, the statistical comparison of the proximate moving averages (block 820) determines whether a difference between the moving averages (i.e., the difference between Average Delta$_t$ and Average Delta$_{t-1}$) has less than or equal to a 1% probability of being random or due solely to chance.

It is then determined whether the most recent moving average Average Delta$_t$ is positive (block 835), and whether the difference between the moving averages is significant (block 840). Where either the difference is insignificant (block 840) or the most recent moving average is not positive (block 835), the process ends (block 850) without reporting an event. Otherwise, where both the difference is significant (block 840) and the most recent moving average is positive (block 835), a detection event is reported (block 845). This includes reporting the x most recent detected outputs. Thus, for example, where x is six, the values corresponding to $TCC_{t-5}$, $TCC_{t-4}$, $TCC_{t-3}$, $TCC_{t-2}$, $TCC_{t-1}$, and $TCC_t$ are all reported. Such reporting may include, but is not limited to, transferring the detection event data from the monitoring device to a central monitoring system. This may include, but is not limited to, transferring the data across a wireless telephone network, across a wired telephone network, across the Internet, across other networks known in the art, and/or combinations thereof.

In conclusion, the present invention provides for novel systems, devices, and methods for monitoring alcohol consumption by human subjects. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for detecting chemical secretions, the method comprising:
   receiving at least a first value and a second value from a chemical sensor attached to a monitored individual;
   calculating a baseline value using at least the first value and the second value; and
   reporting an event when the baseline value is exceeded.

2. The method of claim 1, wherein reporting the event when the baseline value is exceeded includes:
   calculating a difference between the first value and the second to yield a delta value;
   averaging the delta value with previously calculated delta values to yield an average delta value;
   comparing the average delta value with a previously calculated average delta value to yield a significance factor; and
   reporting the event only when the significance factor exceeds the baseline value.

3. The method of claim 1, wherein calculating the baseline value includes:
   calculating a mean value of the plurality of outputs to a confidence of greater than ninety percent.

4. The method of claim 1, wherein the method further comprises filtering the plurality of outputs using one or more filters selected from a group consisting of: a slope filter, a duration filter, and a spike filter.

5. A system, the system comprising:
   a monitoring device attachable to a monitored individual, wherein the monitoring device includes a chemical sensor, a processor, and a non-transitory computer readable medium; and
   wherein the chemical sensor is operable to repeatedly sense a characteristic of the monitored individual to yield a first value corresponding to the characteristic at a first time and a second value corresponding to the characteristic at a second time;
   wherein the non-transitory computer readable medium includes instructions executable by the processor to:
      compare the second value of the chemical sensor with a baseline value, wherein the baseline value is generated based at least in part on the first value; and
      report an event when the baseline value is exceeded.

6. The system of claim 5, wherein the characteristic is a level of alcohol consumed by the monitored individual.

7. The system of claim 5, wherein reporting the event includes reporting a subset of the plurality of the outputs from the chemical sensor.

8. The system of claim 5, wherein reporting the event does not occur until a baseline value is available.

9. The system of claim 5, wherein the generating the baseline value includes calculating the baseline value based at least in part on the first value.

10. The system of claim 9, wherein calculating the baseline value based at least in part on the first value derived from sensing the characteristic of the monitored individual results in a baseline value tailored to the monitored individual.

11. The system of claim 5, wherein generating the baseline value based at least in part on the first value derived from sensing the characteristic of the monitored individual results in a baseline value tailored to the monitored individual.

12. The system of claim 5, wherein the chemical sensor is operable to be attached to one of a first individual and a second individual, and wherein the same algorithm used to generate the baseline value for a first individual is used to calculate the baseline value for a second individual.

13. The system of claim 5, wherein the baseline value is generated based upon an algorithm dependent upon at least one variable received as an input, and wherein the algorithm is independent of one or more variables selected from a group consisting of: the gender of the individual, the weight of the individual, the height of the individual, and food intake of the individual.

14. The system of claim 5, wherein the computer readable medium includes instructions executable by the processor to: perform a slope filter function.

15. The system of claim 5, wherein the computer readable medium includes instructions executable by the processor to: perform a spike filter function.

16. The system of claim 5, wherein the computer readable medium includes instructions executable by the processor to: perform a duration filter function.

17. The system of claim 5, wherein the chemical sensor furtherer yields a third value corresponding to the characteristic at a third time, wherein the computer readable medium further includes instructions executable by the processor to:
calculate a difference between the first value and the third value to yield a delta value;
average the delta value with previously calculated delta values to yield an average delta value; and
compare the average delta value with a previously calculated average delta value to yield a significance factor.

18. The system of claim 17, wherein the event is reported only when the significance factor exceeds the baseline value.

19. The system of claim 5, wherein the baseline value is generated based upon an algorithm, and wherein the algorithm includes:
calculating a mean value of the plurality of outputs to within a defined confidence.

20. The system of claim 19, wherein the defined confidence is greater than ninety percent probability.

21. The system of claim 5, wherein the chemical sensor is a transdermal alcohol sensor.

22. A system, the system comprising:
a monitoring device attachable to a monitored individual configured to take a first alcohol concentration reading at a first time and a second alcohol concentration reading as a second time using a sensor and under direction of a controller; and
a computing device operable to receive at least a subset of the plurality of alcohol concentration readings and to calculate a baseline value using at least the first alcohol concentration reading and the second alcohol concentration reading.

23. The system of claim 22, wherein the sensor is a transdermal alcohol sensor.

* * * * *